United States Patent
Spindler

(10) Patent No.: US 8,071,527 B2
(45) Date of Patent: Dec. 6, 2011

(54) CLEANING COMPOUND FOR CLEANING SURFACES IN A FOOD PROCESSING ENVIRONMENT

(76) Inventor: William E. Spindler, Fort Wayne, IN (US)

(*) Notice: Subject to any disclaimer, the term of this patent is extended or adjusted under 35 U.S.C. 154(b) by 0 days.

(21) Appl. No.: 12/964,834

(22) Filed: Dec. 10, 2010

(65) Prior Publication Data

US 2011/0076340 A1 Mar. 31, 2011

Related U.S. Application Data

(62) Division of application No. 10/607,227, filed on Jun. 26, 2003, now Pat. No. 7,857,913.

(51) Int. Cl.
*C11D 17/04* (2006.01)

(52) U.S. Cl. ........ 510/405; 510/296; 510/439; 510/441; 422/28; 422/32; 206/568

(58) Field of Classification Search .................. 510/405, 510/296, 439, 441; 422/28, 32; 206/568
See application file for complete search history.

(56) References Cited

U.S. PATENT DOCUMENTS

| | | | | |
|---|---|---|---|---|
| 4,390,448 | A * | 6/1983 | Boden et al. | 252/187.26 |
| 5,320,805 | A * | 6/1994 | Kramer et al. | 422/28 |
| 5,739,096 | A * | 4/1998 | Rees | 510/376 |
| 5,739,327 | A * | 4/1998 | Arbogast et al. | 544/163 |
| 5,741,437 | A * | 4/1998 | Arbogast et al. | 252/186.39 |
| 5,877,137 | A * | 3/1999 | Zhou et al. | 510/277 |
| 5,958,289 | A * | 9/1999 | Arbogast et al. | 252/186.39 |
| 5,959,104 | A * | 9/1999 | Arbogast et al. | 544/163 |
| 6,479,454 | B1 * | 11/2002 | Smith et al. | 510/503 |
| 6,479,545 | B1 * | 11/2002 | Levinson et al. | 514/560 |
| 2003/0078178 | A1 * | 4/2003 | Ramirez et al. | 510/309 |

* cited by examiner

*Primary Examiner* — Milton I Cano
*Assistant Examiner* — M. Reza Asdjodi
(74) *Attorney, Agent, or Firm* — Barnes & Thornburg LLP

(57) ABSTRACT

A cleaning compound for cleaning surfaces in a food processing environment includes at least one container, with each container including a peroxide and/or an alkaline reactant therein. The alkaline reactant is selected to raise the pH of the cleaning compound into the alkaline range when the peroxide and the alkaline reactant are mixed together. The cleaning compound may be a liquid or dry compound, which is applied to the surface to be cleaned.

24 Claims, No Drawings

CLEANING COMPOUND FOR CLEANING SURFACES IN A FOOD PROCESSING ENVIRONMENT

RELATED APPLICATIONS

The present application is a Divisional of U.S. patent application Ser. No. 10/607,227, filed on Jun. 26, 2003, entitled, "Cleaning Compound for Cleaning Surfaces in a Food Processing Environment." To the extent not included below, the subject matter disclosed in that application is hereby expressly incorporated into the present application.

BACKGROUND OF THE INVENTION

1. Field of the Invention

The present invention relates to cleaning compounds, and, more particularly, to cleaning compounds for cleaning surfaces in a food processing environment.

2. Description of the Related Art

Numerous chemical compounds exhibit varying degrees of antimicrobial or biocidal activity. Antimicrobial compositions are needed, among other things, to clean and disinfect food surfaces, such as fruits and vegetables, and to clean and disinfect hard-surfaces in the health care industry, food and beverage industries, and households.

Compositions having cleaning and sanitizing effectiveness are known, which include one or more surfactants and one or more antimicrobial agents, where the surfactant is effective at removal of soils, especially soils that contain fats and the antimicrobial agents such as ethylene oxide, strong acids and compositions of aldehydes are known to have varying degrees of biocidal activity. Limitations exist for many of these cleaning compositions in that the antimicrobial agents exhibit toxic, corrosive and irritant properties that limit the compositions usefulness, especially in relation to the food and beverage industries.

Antimicrobial compositions, including lower concentrations of surfactants, resulting in lower corrosion and odor, are also known. For example, U.S. Pat. No. 6,479,454 (Smith et al.) discloses an antimicrobial composition of hydrogen peroxide and amine oxide. Hydrogen peroxide is a known antimicrobial agent, and amine oxide is a high-foaming surfactant. By providing a low concentration mixture of hydrogen peroxide and amine oxide, effective antimicrobial cleaning may occur.

Nonetheless, even with a mixture of hydrogen peroxide and amine oxide at a low concentration as disclosed by Smith et al. '454, the mixture still has a pH in the acid range and thus has higher than desired corrosive effects when applied to surfaces to be cleaned. It is conventionally believed that an antimicrobial compound must be in the acid range to effectively act as an antimicrobial agent. In fact, in line with conventional wisdom, Smith et al. '454 discloses that carboxylic acids may be added to the mixture of hydrogen peroxide and amine oxide to improve the antimicrobial effect. Although such cleaning compounds effectively clean target surfaces; the corrosive properties associated therewith cause substantial operating expense to periodically replace floor and wall surfaces, equipment, etc., damaged by the corrosion.

What is needed in the art is a cleaning compound, which is a hydrogen peroxide donor, which effectively cleans surfaces in a food processing environment without substantial corrosive effects.

SUMMARY OF THE INVENTION

The present invention provides a cleaning compound including a peroxide and an alkaline reactant with a pH in the alkaline range, which effectively cleans surfaces in a food processing environment without substantial corrosive effects.

The invention comprises, in one form thereof, a cleaning compound kit for cleaning surfaces in a food processing environment. The cleaning compound kit includes a first container with hydrogen peroxide therein, and a second container with an alkaline reactant therein. The alkaline reactant is selected to raise the pH of the cleaning compound into the alkaline range when a predetermined amount of the first container and the second container are mixed together.

The invention comprises, in another form thereof, a cleaning compound for cleaning surfaces in a food processing environment. The cleaning compound includes at least one container, with each container including a peroxide and/or an alkaline reactant therein. The alkaline reactant is selected to raise the pH of the cleaning compound into the alkaline range when the peroxide and the alkaline reactant are mixed together.

The invention comprises, in yet another form thereof, a method of cleaning a surface in a food processing environment, including the steps of: providing a cleaning compound consisting essentially of peroxide and an alkaline reactant, the alkaline reactant being selected to raise the pH of the cleaning compound into the alkaline range; and applying the cleaning compound to the surface.

An advantage of the present invention is that surfaces in a food processing environment may be effectively cleaned without substantial corrosive effects.

Another advantage is that the chemical compound may be applied as a liquid or dry compound.

Yet another advantage is that the chemical compound may be provided as a premix or as separate reactants.

DETAILED DESCRIPTION OF THE INVENTION

An antimicrobial cleaning compound of the present invention is used for cleaning surfaces in a food processing environment. The cleaning compound of the present invention provides a potent biocide with minimal corrosive properties. The cleaning compound may be in the form of a cleaning compound kit with separate reactants provided in separate containers, or may be in the form of a single premix with all active ingredients. Regardless whether the cleaning compound is provided as a kit or a premix, the antimicrobial composition effectively reduces the microbial population of surfaces in food processing facilities, such as walls, floors, and equipment. The cleaning compound generally includes a peroxide (peroxygen compound) and an alkaline reactant.

Cleaning Compound Kit Example

In one embodiment of the present invention, a cleaning compound kit includes a first container with hydrogen peroxide therein, and a second container with an alkaline reactant therein. The alkaline reactant is selected to raise the pH of the cleaning compound into the alkaline range when a predetermined amount of the first container and the second container are mixed together. When the hydrogen peroxide and the alkaline reactant are mixed together, the cleaning compound has a pH on the alkaline side (i.e., between approximately 7 to 14 pH).

The hydrogen peroxide ($H_2O_2$) is at a concentration of between approximately 0.1 to 70%, preferably approximately 12%. The hydrogen peroxide also has a pH of between approximately 4.5 to 7, preferably 5.2 pH. As is apparent, the hydrogen peroxide has a pH on the acid side and therefore is corrosive to surfaces on which it is applied.

The alkaline reactant preferably is in the form or mixture of carbonates, phosphates, silicates, borates, hydroxides, etc. The alkaline reactant includes one or more alkaline builders to raise the pH of the cleaning compound into the alkaline range. Specific examples of alkaline builders, which may be included in the alkaline reactant include sodium carbonate and sodium hydroxide. The alkaline reactant preferably has foaming characteristics to assist in removing soil or stains from the surfaces being cleaned. For example, the alkaline reactant may be in the form of a low-foaming, moderate-foaming or high-foaming alkaline cleaner.

The alkaline reactant is contained within the second container at a concentration of between approximately 0.1 to 50%, preferably at a concentration of between approximately 5 to 15%. The alkaline reactant also has a pH of approximately 7 to 14, preferably a pH of between approximately 10 to 13.

The first container and/or the second container can also contain other types of chemical additives, such as chelants, coupling agents, oxygen-stable dyes, and/or oxygen-stable surfactants. A chelant or chelants may be added to control or sequester hardness ions such as calcium and magnesium. In this manner, both detergency and sanitation capability can be enhanced. Coupling agents permit the non-separation of an aqueous alkaline reactant in aqueous liquids.

An example of an oxygen-stable surfactant, which may be added, is amine oxide. Amine oxide is a high-foaming surfactant. Various amine oxides may be utilized for their foaming and surfactant properties. Examples of amine oxides include, but are not limited to: lauryl dimethylamine oxide (commonly available as Ammonyx LO from Stepan Company, or MACAT AO-12 from Mason Chemical), alkyldimethylamine oxide, dialkylmethylamine oxide, alkyldialkoxylamine oxide, dialkylalkoxyamine oxide, dialkyletheramine oxide, and dialkoxyetheramine oxide.

To further improve the foaming of the cleaning compound, diphenyl sulfonate derivatives (such as sodium n-decyl diphenyl oxide di sulfonate) may be added to the cleaning compound as a foam booster to the amine oxides. Examples of commercially available diphenyl sulfonate derivatives are sold under the trade name "Dowfax 3B2" or "Dowfax 2A1." These foam boosters increase the retention time of the cleaning compound on the surfaces to be cleaned, and thereby further improve cleaning. Some other surfactants that are oxygen stable, are Shell Chemical Company's nonionic Neodol 25-7, 25-9, 23-6.5, 91-6 and 91-8, and Stepan's BIO-TERGE PAS-85.

Method of Application of Cleaning Compound Kit

In one example, the first container is in the form of a 55-gallon drum with hydrogen peroxide having approximately a 12% concentration and a pH of approximately 5.2. The second container is in the form of a 55-gallon drum with a high-foaming, alkaline cleaner having a 14% concentration and a pH of approximately 10.2. Depending on the type of surface to be cleaned and soil present, a use dilution of two to eight ounces of the hydrogen peroxide and two to eight ounces of the alkaline reactant is mixed with each gallon of water. When the cleaning compound kit includes hydrogen peroxide, an alkaline reactant and amine oxide, the cleaning compound is mixed at rate of one part amine oxide to between five (5) to 99 parts hydrogen peroxide on an active weight basis, preferably at a rate of one part amine oxide to approximately 9.68 parts hydrogen peroxide by weight. The mixture is then applied to the surface to be cleaned in the food processing environment. For example, the mixture may be foamed onto the surface to be cleaned.

Dry Premix Example

In another embodiment of the invention, a peroxide (rather than hydrogen peroxide) and the alkaline reactant are mixed together in a single container and applied as a dry premix to a surface to be cleaned. In one example, the dry cleaning compound is in the form of sodium percarboriate, also known as sodium carbonate peroxyhydrate. This dry cleaning compound has the chemical formula $Na_2CO_3*1.5H_2O_2$, plus sodium carbonate as a builder. The dry premix may include constituents providing low-foaming and high-foaming capabilities.

Method of Application of Dry Premix

In a dry premix form, the cleaning compound is applied to clean floors and drains using a spreader. The dry premix may also be diluted with water at a rate of four to eight ounces per gallon of water and applied to the surfaces to be cleaned.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A kit that reduces microbial populations on a surface, the kit consisting of:
   a first container consisting essentially of hydrogen peroxide having a corrosive acidic pH; and
   a second container consisting essentially of an alkaline reactant having an alkaline pH;
   wherein either container further includes a component consisting of an amine oxide surfactant;
   wherein the hydrogen peroxide, alkaline reactant and amine oxide surfactant are configured to be combined to form a composition, and raise the pH of the composition from the corrosive acidic pH to the alkaline pH; and
   wherein the composition is configured to reduce microbial populations.

2. The kit of claim 1, wherein the composition has a pH of approximately 7 to 14 when an amount of the first and second containers are mixed together.

3. The kit of claim 1, wherein the hydrogen peroxide is at a concentration of between approximately 0.1 to 70%.

4. The kit of claim 1, wherein the hydrogen peroxide is at a concentration of approximately 12%.

5. The kit of claim 1, wherein the hydrogen peroxide has a pH of between approximately 4.5 to 7.

6. The kit of claim 1, wherein the hydrogen peroxide has a pH of approximately 5.2.

7. The kit of claim 1, wherein the alkaline reactant is either low-foaming, moderate-foaming or high-foaming.

8. The kit of claim 1, wherein the alkaline reactant is selected from a group consisting of carbonates, phosphates, silicates, borates, hydroxides.

9. The kit of claim 1, wherein either the first or second container also includes at least one of a chelant, coupling agent, or oxygen-stable dye.

10. The kit of claim 1, wherein the alkaline reactant is at a concentration of between approximately 0.1 to 50%.

11. The kit of claim 1, wherein the alkaline reactant is at a concentration of between approximately 5 to 15%.

12. The kit of claim 1, wherein the alkaline reactant has a pH of between approximately 7 to 14.

13. The kit of claim 1, wherein the alkaline reactant has a pH of between approximately 10 to 13.

14. The kit of claim 1, wherein the composition is mixed at a rate of one part amine oxide to between 5 and 99 parts hydrogen peroxide on an active weight basis.

15. The kit of claim 14, wherein the composition is mixed at a rate of one part amine oxide to approximately 9.68 parts hydrogen peroxide on an active weight basis.

16. The kit of claim 1, wherein the amine oxide surfactant is adiphenyl sulfonate derivative.

17. A kit that reduces microbial populations on a surface, the kit consisting of:
  a first container consisting essentially of hydrogen peroxide having a corrosive acidic pH; and
  a second container consisting essentially of an alkaline reactant having an alkaline pH;
  wherein either container further includes a component consisting of at least one oxygen-stable surfactant;
  wherein the hydrogen peroxide, alkaline reactant and oxygen-stable surfactant are configured to be combined to form a composition and raise the pH of the composition from the corrosive acidic pH to the alkaline pH; and
  wherein the composition is configured to reduce microbial populations.

18. The kit of claim 17, wherein the kit further consists of at least one chelant.

19. The kit of claim 17, wherein the kit further consists of at least one chelant and at least one coupling agent.

20. The kit of claim 17, wherein the kit further consists of at least one chelant, at least one coupling agent and at least one oxygen-stable dye.

21. The kit of claim 17, wherein kit further consists of at least one coupling agent.

22. The kit of claim 17, wherein the kit further consists of at least one oxygen-stable dye.

23. The kit of claim 17, wherein the kit consists of at least one chelant and at least one oxygen-stable dye.

24. The kit of claim 17, wherein the kit further consists of at least one coupling agent and at least one oxygen-stable dye.

* * * * *